US005565355A

United States Patent [19]

Smith

[11] Patent Number: 5,565,355
[45] Date of Patent: Oct. 15, 1996

[54] GROWTH MEDIUM

[75] Inventor: Dale R. Smith, Rotorua, New Zealand

[73] Assignee: New Zealand Forest Research Institute Limited, Rotorua, New Zealand

[21] Appl. No.: 219,879

[22] Filed: Mar. 30, 1994

Related U.S. Application Data

[63] Continuation-in-part of Ser. No. 993,688, Dec. 21, 1992, abandoned.

[30] Foreign Application Priority Data

Dec. 19, 1991 [NZ] New Zealand ............................ 241077

[51] Int. Cl.$^6$ ............................... A01H 4/00; A01H 7/00; C12N 5/04
[52] U.S. Cl. ................. 435/240.49; 435/240.45; 435/240.48; 435/240.5; 800/200; 800/DIG. 49; 800/DIG. 50; 800/DIG. 51
[58] Field of Search ............................ 435/240.4, 240.45, 435/240.49, 240.50; 800/200, 205, DIG. 49, DIG. 50, DIG. 51

[56] References Cited

U.S. PATENT DOCUMENTS 5,035,007  7/1991  Gupta et al. ........................ 435/240.45

OTHER PUBLICATIONS

Gamborg "Cell Culture and Somatic Cell Genetics of Plants" vol. 1 Academic Press, Chapter 3, pp. 18–35.

Troncoso et al. "Growth and mineral composition of grape vine rootstock cultured in vitro with different levels of ammoniun nitrate." Plant Nutrition—physiology and application, pp. 653–654.

Primary Examiner—Gary Benzion
Attorney, Agent, or Firm—Abelman, Frayne & Schwab

[57] ABSTRACT

This invention relates to growth media for capturing and sustaining the growth of conifer embryogenic tissue and conifer embryos.

Using media of the invention allows good growth of embryogenic tissue and conifer embryos which can subsequently be germinated to obtain plants. With these media there is no need to use plant regulator/hormones such as auxins and/or cytokinins for embryogenic tissue cature and maintenance.

34 Claims, No Drawings

GROWTH MEDIUM

This application is a continuation-in-part of my earlier application Ser. No. 07/993,688 filed Dec. 21, 1992, now abandoned, which is hereby incorporated by reference.

This invention relates to a growth medium embryogenic tissue.

BACKGROUND TO THE INVENTION

A basic medium commonly used for capturing and sustaining the growth of plant embryogenic tissue is known as the Murashige Skoog (MS) medium. This medium is based on the ratios and concentrations of minerals found in tobacco leaves. It has been possible to successfully grow embryogenic tissue from many species in media which have slight variations from the concentrations/ratio of the minerals in the MS medium. Unfortunately, the MS medium or variations are not ideal for growing coniferous tissue.

One growth medium known as the Weyerhaeuser medium (Gupta and Pullman 1990, 1991a, 1991b) has been developed particularly for coniferous embryogenic tissue, based on chemical analysis of the composition of pine seeds. This medium is significantly different from the MS medium in both its ratios and concentrations. Unfortunately the Weyerhaeuser medium only works in relation to a few conifer genotypes and therefore is too specific for general conifer propagation. There are other problems associated with the Weyerhaeuser medium and the media referred to above which will become apparent from the following discussions.

With embryogenesis, an aim is to obtain as many embryos as possible from a single seed. The natural growth of a seed proceeds in six main stages:

a) The first stage has an embryo consisting of between one to three cells attached to the archegonium and positioned within the corrosion cavity of the seed.

b) The second stage has a number of embryos multiplying and developing with each embryo having less than 64 cells. It is usually at this stage (zygotic polyembryogenesis) that embryos are placed onto or into the growth medium.

c) The third stage is growth of the embryo away from the archegonium and towards the end of the corrosion cavity. The long axis of the embryo develops and assumes a cylindrical shape with a complex of elongated cells, the suspensors, at one end, and with a rounded head at the other end where the apical meristem will eventualy develop. This is known as a bullet stage.

d) The fourth stage is the development of cotyledonary tissue at the apex of the embryo, at the root end of which is a group of cells known as the suspensor zone.

e) The fifth stage is the further development and maturation of embryos, with the formation and greening of cotyledons, formation of an epicotyl or shoot apex, and formation of a hypocotyl. This stage of development ends with emergence of a root (radicle), that is, the process of germination.

f) The sixth stage is the establishment of the germinated embryo as a plant capable of growth in soil.

Prior growth media do not encourage the natural zygotic polyembryogenic state which occurs in the seeds. Instead, with the previous media it has necessary to dissect out embryos at the cotyledonary stage. Plant growth regulators (hormones) are then applied to the cells of the body of the embryo or at the point of attachment of the suspensor to encourage the cells to differentiate back to nonspecialized cells which can then be multiplied. This process, often referred to in the literature as somatic embryogenesis, has been widely reported for *Picea* (Spruce) species, and to a lesser degree for other conifers.

One problem with the above process is that there is in effect double handling involving first the development of specialised tissue, reversion of same to basic cell types and then re-growth of the tissue to form mature embryos. Another problem is that the growth hormones used (such as 2,4-D) may induce somaclonal variation. That is, the ideal genotype which is being cloned may be corrupted by the growth hormones and the resultant embryo may not be true to type.

It is an object of the present invention to address the above problems, or at least to provide the public with a useful choice.

Further objects and advantages of the present invention will become apparent from the following-description.

SUMMARY OF THE INVENTION

According to one aspect the present invention comprises growth media effective for capturing and sustaining the growth of embryogenic tissue and for subsequent development, maturation and germination of conifer embryos, including inorganic ions within the concentration ranges given in Table 1:

TABLE 1

| ION | CONCENTRATION RANGE mmoles/l |
|---|---|
| $NO_3$ | 8–27 |
| $NH_4$ | 0.95–3 |
| Ca | 0.08–0.25 |
| Fe | 0.05–0.15 |
| Na | 1.9–5.75 |
| Zn | 0.045–0.135 |
| Cu | $4.5 \times 10^{-3}$–$1.5 \times 10^{-2}$ |
| Mg | 0.8–2.5 |

It should be appreciated that the growth medium may be prepared in liquid or solid form.

Reference throughout this specification will be made to the use of the present invention with respect to embryogenic tissue from conifer such as *Pinus radiata, Pinus taeda, Pinus elliotii,* and *Pseudotsuga menziesii,* however it should be appreciated that the present invention may be able to be used with embryogenic tissue coming from other conifers.

A medium produced in accordance with the present invention provides an environment for the embryos to grow in and the applicant has found that a number of distinctive advantages have arisen.

The first advantage is that the present invention provides for sustained zygotic polyembryogeny in-vitro. Unlike the situation with the previous media, it is generally no longer necessary to dissect embryos at the late pre-cotyledonary stage out of seed nor is it necessary to apply growth hormones. When using a medium of the present invention, the embryogenic tissue grows out of the seed naturally, as illustrated in the examples herein.

Another advantage of the present invention is that the medium is suitable for growing a high percentage of genotypes.

According to another aspect the invention provides a method of growing embryogenic tissue comprising the step of growing the tissue on a growth medium as described above.

The medium and method of the invention are particularly suitable for capturing and sustaining the growth in vitro of embryogenic tissue of conifers in particular, including *Pinus radiata, Pintus taeda, Pinus elliotii* and *Pseudotsuga manziestii*, for example.

The medium and method of the invention are also particularly suitable for the development, maturation and germination of somatic embryos of conifers in particular including *Pinus radiata, Pinus taeda, Pinus elliotii* and *Pseudotsuga menziesii*, for example.

a general tissue culture medium for radiata pine improved at New Zealand Forest Research Institute Limited, Rotorua, New Zealand and referred to as FRI-LP. It can be seen again that there are distinct differences between the concentration of ions in the preferred medium and in the previous media.

Previously it was thought that a relatively high level of calcium was required in growth media, however the level of calcium in the preferred medium in Table 3 has been effective for many coniferous genotypes. Another noticeable difference between the preferred medium and the prior art media is the higher level of sodium, copper and zinc in the preferred medium.

TABLE 3

MEDIA ION CONCENTRATION COMPARISON (mmoles/l)

| ION | PREFERRED MEDIUM | WEYERHAEUSER MEDIUM | MURASHIGE SKOOG MEDIUM | FRI-LP MEDIUM |
|---|---|---|---|---|
| NO3 | 17.80 | 20.54 | 39.40 | 32.96 |
| NH4 | 1.96 | 7.54 | 20.61 | 5.00 |
| TOTAL N | 19.76 | 28.09 | 60.02 | 37.96 |
| P | 1.96 | 1.00 | 1.25 | 1.98 |
| K | 14.16 | 10.02 | 20.05 | 19.79 |
| Ca | 0.17 | 1.00 | 2.99 | 5.08 |
| Mg | 1.62 | 2.50 | 1.50 | 1.46 |
| Cl | $3.42 \times 10^{-1}$ | 1.00 | 5.99 | $2.10 \times 10^{4}$ |
| Fe | 0.10 | 0.02 | 0.10 | 0.11 |
| S | 1.83 | 1.14 | 1.73 | 1.69 |
| Na | 3.85 | 0.06 | 0.20 | 0.22 |
| B | 0.13 | 0.25 | 0.10 | 0.10 |
| Mn | $1.62 \times 10^{-2}$ | $6.21 \times 10^{-2}$ | $1.00 \times 10^{1}$ | $8.97 \times 10^{-2}$ |
| Zn | 0.09 | 0.05 | 0.03 | 0.03 |
| Cu | $9.61 \times 10^{-3}$ | $5.01 \times 10^{-4}$ | $1.00 \times 10^{-4}$ | $1.00 \times 10^{-3}$ |
| Mo | $8.27 \times 10^{-4}$ | $5.17 \times 10^{-4}$ | $1.03 \times 10^{-3}$ | $1.03 \times 10^{-3}$ |
| Co | $8.41 \times 10^{-4}$ | $5.25 \times 10^{-4}$ | $1.05 \times 10^{-4}$ | $1.05 \times 10^{-4}$ |
| I | $6.02 \times 10^{-3}$ | $2.50 \times 10^{-2}$ | $5.00 \times 10^{-3}$ | $4.82 \times 10^{-4}$ |

DETAILED DESCRIPTION OF THE INVENTION

The medium of the invention comprises ions within the concentration ranges of Table 1 above, which are given again in column A of Table 2 below while column B gives preferred ranges for the ion concentrations and column C gives ion concentrations of one particularly preferred medium. Ion concentrations within 5% of those of column C are also highly preferred.

TABLE 2

MEDIA ION CONCENTRATIONS (mmoles/l)

| ION | A | B | C |
|---|---|---|---|
| NO3 | 8–27 | 13–23 | 17.8 |
| NH4 | 0.95–3 | 1.5–2.5 | 1.96 |
| Ca | 0.08–0.25 | 0.12–0.21 | 0.17 |
| Fe | 0.05–0.15 | 0.07–0.13 | 0.10 |
| Na | 1.9–5.75 | 2.9–4.9 | 3.85 |
| Zn | 0.045–0.135 | 0.006–0.12 | 0.09 |
| Cu | $4.5 \times 10^{-3}$–$1.5 \times 10^{-2}$ | $7 \times 10^{-3}$–$1.2 \times 10^{-2}$ | $9.61 \times 10^{3}$ |
| Mg | 0.8–2.5 | 1.2–2.0 | 1.62 |

Table 3 provides a comparison between the ion concentrations of one preferred medium of the invention with the Weyerhaeuser medium, the Murashige Skoog, medium and It should be appreciated that the composition of the preferred medium above is given by way of example only and that other ratios and concentrations may be used, within the ranges of Table 1 above.

It is the concentrations of the inorganic ions listed in Table 1 which distinguish media of the invention from other media such that the medium of the invention is able to sustain the growth and proliferation of embryogenic tissue of a wide range of conifer types. Potassium, chloride, phosphate, manganese, borate, sulphate, iodine, molybdenum and cobalt ions are preferably including in the medium. The media of the invention peferably also contain other nutrients generally used in conifer embryogenesis such as a carbon source. In the preferred media vitamins especially thiamine, nicotinic acid, and pyridoxinc are preferably also included. Isositol, sucrose, agar and glutamine and other amino acids (particularly asparagine, arginine, citrulline, ornithine, lysine, alanine and proline) are also preferably present in preferred media. the concentrations of some of the other components can usefully be varied according to the stage of the embryogenesis. For example it is preferred to include glutamine and other amino acids in relatively high concentrations for the later stages of embryogenesis. Particularly preferred media include those of the solutions of Tables A5 to A9 at the end of this disclosure. Also preferred are media of the invention having concentration of the nondistinguishing components at levels between 50% and 150% of those found in Tables A5 to A9. Highly preferred are media with concentrations of the non-distinguishing components at 75% to 125% of those found in the solutions of Table A5 to A9. The preferred pH for media of the invention is in the range 5.5–5.9. Agar may be included in preferred media at 0.5–1.5 g/l (w/v). Sucrose may be included in preferred media at 5–50 g/l (w/v).

According to another aspect of the invention there is provided a process for conifer embryogenic tissue capture and embryogenic tissue maintenance. In embryogenic tissue capture it is preferred that the seeds are surface sterilised and entire megagametphytes containing the immature zygotic embryos are dissected and placed directly onto a medium of the invention. The medium shown in Table A5 is particularly preferred for this. Culture is carried out at an appropriate light intensity. Ambient photo period is preferably used and the temperature is preferably about 24° C. It is preferred that plant growth regulators such as auxins and cytokinins are not present. Preferred species for the practice of the invention include *Pseudotsuga menziesii, Pinus taeda, Pinus elliotii* and *Pinus radiata*.

Embryogenic tissue will grow for up to a month on the capture medium but for sustained maintenance it is recommended that conifer embryogenic tissue is maintained on standard embryogenesis medium (Table A6). Again for the maintenance of conifer embryogenic tissue it is preferred not to use auxins or cytokinins.

In one embodiment of the present invention a growth medium may be used having the same ratios of ions as shown for the preferred medium in Table 3 but with a different overall ion concentration. For instance, at the zygotic polyembryogenesis stage of the embryo development (stage b above) a medium may be used which has only half of the concentration of each of the ions listed for the preferred medium in Table 3 (eg see Table A5). The tissue may be grown on this medium until a sustained extragametophytic growth of tissue has been established and can be relocated on full strength medium such as that of Table A6. Again it is noted that the level of calcium is an important factor with respect to a growth medium suitable for growing embryogenic tissue either at stage b or at later stages.

The growth medium may also contain 4–9 gm/l of gellan gum. Media of this embodiment have been found to be particularly useful for conifer embryo maturation. The gellan gum marketed under the name Gelrite™ has been found to be particularly useful. Transfer from embryo development medium with conventional Gelrite content of about 3 gm/l to an embryo maturation medium with 5–7 gm/l (preferably 6 gm/l) Gelrite followed by subsequent transfer to another embryo maturation medium differing in that the Gelrite concentration was 4–5 gm/l (preferably 4.5 gm/l Gelrite) gave surprisingly good yields of embryos. It appears that transient use of very high Gelrite levels (eg 6 gm/l) stimulates the maturation of somatic embryos.

Water vapour permeable films or filters may be used in conjunction with the medium of the invention. Use of such films or filters in embryogenesis has been described in co-pending application Ser. No. 991,994 filed Dec. 17, 1992. Using water vapour permeable films or filters allows the avoidance of buildup of condensation. Thus, problems such as those relating to the presence of freely available liquid on the surface of solid media are avoided. Also the films or filters allow a controlled rate of water loss. This is perferably in the range of 90–150 gm/sq meter per day. A rate particularly suitable for *Pinus radiata* embryos is 118 gm/sq meter per day. Many types films may be used provided they have desired qualities of being able to seal against microbial infection and are sufficently permeable to water vapour. For instance, the film may be made from plastics material such as polyvinyl chloride (PVC). Among those films suitable are those sold under the trade mark VITAFILM by the Goodyear Tire & Rubber Co (Australia) Ltd. In this range the OMNI, VW, MWT and F10 V/S are all useful with the medium of the invention for conifer embryogenesis.

When the somatic embryos maturing on the medium of the invention are in vessels covered with a water permeable film, evaporation of liquid from the medium makes it less available to the embryos, mimicking the changes in matric potential that occur during natural embryo development. As a consequence of the loss of water, the concentration of ions within the medium increases, however without taking it outside the range useful for embryogenesis. I have been unable to duplicate the beneficial effect of the water permeable film simply by transferring embryos to medium with higher concentration of medium components equivalent to that attained when water vapour is lost through a water permeable film. I have concluded therefore that the beneficial effect of the use of water permeable film is not due to an increase in osmotic potential of the medium, or to the increase in concentration of substrate such as sucrose. I believe rather that the effect of the film is to decrease the availability of water to the developing embryo at a precise and critical stage of maturation.

According to another aspect of the invention there is provided a process for harvest of mature embryos with developed cotyledons, and subsequently treating them to allow a high percentage of germination, such that the conversion of cotyledonary stage embryos to plants growing in soil averages or exceeds 50%. Conversion of somatic embryos to plants at an efficiency approaching that necessary for the commercial application of somatic embryogenesis has not been previously reported for conifers other than spruces. Germination is preferably carried out on media with inorganic ions at concentrations of 50% to 100% of those listed in Table 2, column C and Table 3. Particularly preferred for this is the medium of Table A10.

EXAMPLES

The following Examples further illustrate the invention. The Examples illustrate the use of the medium in embryogenic tissue capture and in embryogenic tissue maintenance for capture and maintenance of embryogenic tissue of *Pseudotsuga menziesii, Pinus taeda, Pinus elliotii* and *Pinus radiata* and for subsequent embryo development and maturation, and subsequent germination and conversion to plants in soil.

Standard procedures for the preparation of plant tissue culture media are followed. Media as described below are sterilised by autoclaving for 20 minutes at 121° C. Organic components are filter sterilised, and are added to the medium after autoclaving. Culture is carried out in 90 mm petri dishes each containing 22 ml of medium.

EXAMPLE 1 - EMBRYOGENIC TISSUE CAPTURE

Seeds were removed from cones of *Pinus radiata, Pinus taeda, Pinus elliotii*, and *Pseudotsuga menziesii* at an appropriate stage of development of the zygotic embryos (for instance for *Pinus radiata* in New Zealand, from early December to early January), and the seeds were surface sterilised and entire megagametophytes containing the immature zygotic embryos were dissected and placed directly onto Standard Embryogenic Tissue Capture Medium (Table A 5). Dishes were cultured at low light intensity (5 microEinsteins $m^{-2}$ $sec^{-1}$) under ambient photoperiod. The temperature was maintained constant throughout at 24° C. +/–1° C.

As a variation, zygotic embryos at any stage of development up to the formation of cotyledonary primordium formation may be dissected and placed directly onto Standard Embryogenic Tissue Capture Medium (Table A5), or onto Standard Embryogenesis Medium (Table A6) or Embryo Development Medium (Table A7).

Embryogenic tissue grew out onto the medium over the next three months, and tissue pieces greater than 2 millimeters across were transferred to Standard Embryogenesis Medium.

Embryogenic tissue grew out onto the medium over the next three months, and tissue pieces greater than 2 millimeters across were transferred to Standard Embryogenesis Medium.

This protocol differs from that described by other authors, for example in the patents granted to Gupta et. al (1990, 1991a, 1991b), and in the references cited therein. The major difference is that the mineral salt composition differs markedly from that used by the above named authors, and in the references which they cite (see Table 3).

The mineral salt formula of this invention allows the capture of embryogenic tissue without the need to resort tot the use of plant growth regulators such as auxins (eg. 2,4-Dichlorophenoxy acetic acid, Indole -3- acetic acid, 1—Napthylacetic acid, or Indole-butyric-acid) and/or cytokinins (eg. 6-Benzylamino Purine, Zeatin, or N6-[2 Isopenetenyl]adenine). While plant growth regulators such as auxins or cytokinins may on occasions enhance the growth of tissue on the Standard Embryogenic tissue Capture Medium, the Standard Embryogenesis Medium or the Embryo Development Medium, their use is not essential when explants are put into culture at the appropriate stage of development of the immature zygotic embryo.

The simple protocol described has been successfully used to capture embryogenic tissue of *Pseudotsuga menziesii, Pinus taeda, Pinus elliotii,* and *Pinus radiata* without need to alter the protocol an any way for each of the above named species. 15500 explants from 10 different control pollinated cone parents of *Pinus radiata* were put into culture on the Standard Embryogenic Tissue Capture Medium and after adjustment of results for contamination, up to 100% of the whole megagametophyte explants gave rise to embryogenic tissue, when the tissue placed into culture was developmentally competent to form embryogenic tissue. The mean response of the best result for each cone parent was 32.9% for *Pinus radiata*. For *Pinus taeda, Pinus elliotii* and *Pseudotsuga menziesii* about 30% of megagametophyte explants at an appropriate stage of development gave rise to embryogenic tissue.

EXAMPLE 2 - EMBRYOGENIC TISSUE MAINTENANCE

Embryogenic tissue has been found to continue to grow for up to a month on the Standard Embryogenic Tissue Capture Medium, however this medium is unsuitable for sustained tissue maintenance. The conifer embryogenic tissue was more effectively maintained on Standard Embryogenesis Medium (Table A6).

Tissue development was maintained in a primitive state on Standard Embryogenesis Medium, ideally with embryos never developing past the eight-celled stage before dissociating into simple embryonic initials. These embryos may have a single suspensor cell attached to the embryo initial - further development of suspensors is not encouraged on this medium, and the tissue does not become "bulky".

2.1 Plant growth regulators

This protocol for the maintenance of conifer embryogenic tissue differs from that described by other authors, for example in the patents granted to Gupta et. al (1990, 1991a, 1991b ), and in the references cited therein. The major difference is that the mineral salt composition differs markedly from that used by the above named authors, and in the references which they cite.

The ion composition of the medium that is described here allows the maintenance of embryogenic tissue of conifers without the need to resort to the use of plant growth regulators such as auxins (eg. 2,4-Dichlorophenoxy acetic acid, Indole -3- acetic acid, 1-Napthylacetic acid, or Indolebutyric-acid) and/or cytokinins (eg. 6-Benzylamino Purine, Zeatin, or N6-[2 Isopentenyl]adenine).

Plant growth regulators such as 2,4-D and BAP may stimulate apparent growth of embryogenic tissue, in part due to formation of suspensor cells, but the use of plant growth regulators is not necessary, and confers no benefits. While we have recovered sound, mature somatic embryos from some cell lines maintained on medium with 2,4-D and BAP, my experience has been that these cell lines lose their plant-forming potential much sooner than the same cell lines which have been maintained on the Standard Embryogenesis Medium without plant growth regulators.

It is usually the experience of practitioners of the art of somatic embryogenesis of conifers that cell lines quickly lose the ability to form mature embryos, and subsequently plants.

The ability to retain the plant-forming potential of conifer cell lines for periods of in excess of one year is a benefit of the use of the unique mineral salt composition which is described here. This benefit is possibly due to the fact that plant growth regulators are not required for embryogenic tissue capture and maintenance in the medium described herein. Most cell-lines grown on the preferred medium showed ill-thrift or died when placed on the Weyerhaeuser medium.

EXAMPLE 3 - EMBRYO DEVELOPMENT

Embryo development was encouraged by transfer of tissue to an Embryo Development Medium (Table A7). Embryogenic tissue from the maintenance medium was suspended in liquid medium in a sterile McCartney bottle. Embryogenic tissue was used at the rate of 1 gm per 4 ml of Cell Suspension Medium (Standard Embryogenesis Medium with the agar omitted). When the suspension was finely divided, it was dispensed as 0.25 ml aliquots, three per 90 mm. petri dish containing Embryo Development Medium which consisted generally of Standard Embryogenic Tissue Maintenance Medium to which was added amino acids including glutamine at 550 mg/l, and which was gelled with 3.0 gm/l Gelrite rather than with Difco Bacto agar (see Table A7).

The first step in somatic embryo development is marked by the continued multiplication of the cells in an individual embryo to form a compact mass, often referred to in the literature as the "proembryo" or "proembryonic mass". It is roughly equivalent to the "globular" stage of development in dicotyledonous angiosperms. As this embryo mass forms, the single suspensor cell develops into a multi-stranded structure, also called the suspensor. The embryo head continues to develop, and assumes a cylindrical shape with a rounded head. This stage is sometimes referred to in the literature as the "bullet" stage.

Culture dishes were incubated under the same conditions as the maintenance stage. Over approximately 2 to 3 weeks the tissue rapidly increased in bulk, and took on a "spiky" appearance. Over the next 2 to 3 weeks, "bullet" stage embryos with well defined suspensors became readily visible to the unaided eye. At this point, the tissue masses were subdivided, and are transferred to Embryo Maturation Medium.

EXAMPLE 4 - EMBRYO MATURATION

Each "spot" of tissue on the Embryo Development Medium which was judged to be at a suitable stage of development was subdivided and the pieces transferred to Embryo Maturation Medium # 1 (Table A8). Embryo Maturation Medium # 1 is similar to Embryo Development Medium, but contains higher concentrations of amino acid, such as glutamine at 5–10 gm/l, Abscisic acid in the range 5 mg/l, and Gelrite at a concentration between 4.5 gm/l and 6 gm/l. A concentration of 6 gm/l, is the preferred level of Gelrite for the first transfer from Embryo Development Medium to Embryo Maturation Medium (refer Table A8).

The usefulness of manipulating the Gelrite levels in this manner is illustrated by the following experiments.

Embryogenic tissue of a competent plant-forming clone of *Pinus radiata* was transferred from Embryo Development Medium onto Embryo Maturation Medium #1 gelled with 8 grams/liter Difco Bacto agar, or 3 grams/liter gellan gum (Gelrite™) or 6 grams/liter gellan gum. Each treatment had eight replicate dishes. The yield of harvestable somatic embryos, capable of germination and conversion to plants was assessed when embryo production ceased after six weeks. Results are shown in Table 4.

TABLE 4

| Treatment | Total number of embryos | Average yield per dish |
|---|---|---|
| 8 g/l Bacto agar | 0 | 0.0 |
| 3 g/l Gelrite ™ | 16 | 2.0 |
| 6 g/l Gelrite ™ | 141 | 17.6 |

As a refinement to this protocol, I have found that it is useful to further enhance embryo yield by removing the tissue from Embryo Maturation Medium #1 with 6 grams/liter Gelrite after three weeks, and placing subdivided tissue pieces onto Embryo Maturation Medium #2 with 4.5 grams/liter Gelrite. FIG. 1 illustrates a maturation protocol taking advantage of these effects and those obtained from the use of water vapour permeable films.

EXAMPLE 5 - THE EFFECT OF USE OF WATER VAPOUR-PERMEABLE FILMS ON EMBRYO MATURATION

This example illustrates the use of water vapour permeable films on yield of embryos obtained from culture on the medium of the invention. Tissue of a plant-forming *Pinus radiata* embryogenic cell line was distributed in equal amounts at random over a number of petri dishes containing the EMM#1 medium as described in Table A8. Some of the dishes retained plastic lids which were sealed at the margins with impermeable domestic cling film. Other dishes were instead covered with one of four different plastic films. In this experiment, over a period of ten days cotyledonary stage somatic embryos were harvested directly from EMM#1 (Table A8). The results are shown in Table 5 below. Each treatment had four dishes of embryo-forming tissue. The use of Vitafilm Omni-film produced the greatest yield of somatic embryos for this particular cell line in this experiment.

TABLE 5

The effect of permeable films on the yield of somatic embryos.

| Film/Closure | Total number of somatic embryos | Average somatic embryos per dish |
|---|---|---|
| Plastic petri dish lid/cling film | 28 | 7.0 |
| Vitafilm F10 V/S | 51 | 12.7 |
| Vitafilm VW | 62 | 15.5 |
| Vitafilm Omni-film | 97 | 24.2 |
| Vitafilm MWT | 50 | 12.5 |

EXAMPLE 6 THE EFFECT OF FILMS ON WATER LOSS FROM GROWTH MEDIUM IN PETRI DISHES.

Petri dishes containing solid somatic embryo development medium were covered with plastic lids, sealed on with cling film, or with one of four different gas permeable plastic films. Initial weights of the dishes were recorded, and weight loss noted at intervals of 2–3 days. There were four replicates of each treatment, and dishes were maintained in a 24° C. incubator under the same conditions as used for somatic embryo development.

The mean water loss from dishes after 9 days when covered with lids of different films was determined. Water loss was correlated with the somatic embryo counts from identical dishes of medium cultured under the same conditional A correlation between embryo formation and water loss of 0.994 was determined statistically for the film covered dishes. Experimental results are shown in Table 6.

TABLE 6

Embryo formation and water loss from media

| Lid/Film | Number of Embryos | Water Loss (gm/9 days) |
|---|---|---|
| Lid | 28 | 0 |
| Vitafilm F10 V/S | 51 | 4.88 |
| Vitafilm VW | 62 | 5.14 |
| Vitafilm Omni-film | 97 | 6.73 |
| Vitafilm MWT | 50 | 4.60 |

The water loss from dishes giving the highest yield of somatic embryos, that is those covered with Vitafilm Omni-film, was determined to be 118 $g/m^2$ dish area/day.

In another experiment, following approximately three weeks of culture om EMM#1, tissue of four plant-forming *Pinus radiata* embryogenic cell lines was subdivided and distributed in equal amounts at random over a number of petri dishes containing the EMM#2 medium which had Gelrite at 4.5 gm/l as described in Table A9. Some of the dishes retained plastic lids which were sealed at the margins with impermeable domestic cling film. Other dishes were instead covered with one of two different plastic films. As an additional treatment, lidded, sealed dishes contained an ethylene absorbing agent (potassium permanganate on a matrix of aluminum oxide). After a period of eight days, cotyledonary stage somatic embryos were harvested. The results are shown in Table 7 below. Each treatment had four dishes of embryo forming tissue.

TABLE 7

The effect of permeable films on yield of cotyledonary stage somatic embryos.

| Cell Line | Treatment | Mean embryos per dish | 5% LSD test |
|---|---|---|---|
| I22 | Standard dish | 14.5 | b |
| | Vitafilm Omnifilm | 78.0 | a |
| | Vitafilm MWT 380 | 110.0 | a |
| | Ethylene absorber | 26.5 | b |
| I25 | Standard dish | 4.0 | b |
| | Vitafilm Omnifilm | 17.0 | a |
| | Vitafilm MST 380 | 14.5 | a |
| | Ethylene absorber | 5.0 | b |
| A13 | Standard dish | 1.0 | b |
| | Vitafilm Omnifilm | 6.5 | ab |
| | Vitafilm MWT 380 | 9.5 | a |
| | Ethylene absorber | 2.0 | ab |
| A17 | Standard dish | 1.5 | a |
| | Vitafilm Omnifilm | 1.0 | a |
| | Vitafilm MWT 380 | 0.5 | a |
| | Ethylene absorber | 0.5 | a | a,b Difference in results of treatments bearing the same letter were not statistically significant.

The results in Table 7 indicate that the use of water-permeable films in the EMM#2 stage enhances the production of cotyledonary stage somatic embryos, and also that there is probably an optimal rate of water loss appropriate to each plant cell line (clone) when grown on EMM#2. These results also show that up to more than 100 embryos at the cotyledonary stage may be obtained from a single petri dish for Pinus radiata. With Pinus taeda the results of this step are similar with as many as 10–20 embryos at the cotyledonary stage being produced per dish.

EXAMPLE 7 - RECOVERY OF PLANTS FROM SOMATIC EMBRYOS

Well developed somatic embryos were transferred to NZ FRI Embryo Germination Medium (Table A10). Dishes were sealed with clingfilm and maintained under 50% shade cloth in standard incubator conditions. Embryos were incubated at 24+/−1 degree Celsius, under a light intensity of approximately 40 micro Einsteins $m^{-2}$ $sec^{-1}$, and a 16-hour photoperiod.

For somatic embryos from new cell lines, roots appeared as early as 10 days after transfer to Germination Medium. As cell lines age, roots took longer to emerge but usually appeared within 12 weeks.

New cell lines produced many somatic embryos of high quality. Generally, these were dark green, had long cotyledons, and normally formed a definite epicotyl while still in sterile culture. Embryos of this type tend to form roots quickly, and a high conversion efficiency (percentage of harvested mature cotyledonary stage embryos converting to plants in soil, greater than 50%) is observed. I have observed that the growth and quality of plants is directly related to the quality of the epicotyl at time of pricking-out of embryos into progation medium. Somatic embryos with very short epicotyls do not perform as well as those which have well developed shoots of 5 mm of longer, It is likely that the cotyledons of somatic embryos do not function as photosynthetic organs, and that the embryos rely on the epicotyl for carbon fixation in-vivo.

Setting of Germinated Embryos

Germinated somatic embryos were set under ambient glasshouse conditions into 350 mm×295 mm×55 mm nursery flats containing the following propagation medium:

1.5 parts fine peat 1.0 parts perlite 0.5 parts fine pumice

Diazinon, ½ teaspoon per tray

Magnesium ammonium phosphate 30 gm per tray

Normal nursery procedures for the exflasking of tissue cultured plant material are followed subsequently.

The protocols described above, using he unique mineral salt medium described in Table 3 have been used to capture embryogenic tissue from whole megagametophyte explants of Pinus radiata, Pinus taeda, Pinus elliotii, and Pseudotsuga menziesii using the Standard Embryogenic Tissue Capture Medium described in Table A5. This medium has proved to be satisfactory for all the conifer species named above without alteration. Embryogenic tissue of Pinus radiata, Pinus taeda, Pinus elliotii, and Pseudotsuga menziesii has been proliferated and maintained, often for periods of several years, by regular 14 day transfers to fresh dishes of Standard Embryogenesis Medium as described in Table A6. This medium has proved to be of use for there four species without alteration.

Embryogenic tissue of Pinus radiata, Pinus taeda, Pinus elliotii, and Pseudotsuga menziesii has been proliferated and the formation of "Bullet" stage somatic embryos has been observed upon transfers to Embryo Development Medium as described in Table A7. This medium has proved to be of use for these four species without alteration.

Mature somatic embryos have been observed on EMM#1 and EMM#2. Several thousand mature cotyledonary stage somatic embryos of over 50 clones of Pinus radiata have been harvested from these media and transferred via standard germination and nursery procedures to soil. Over 4000 plants from 50 clones of Pinus radiata have been grown in soil in the greenhouse, nursery bed, or in field trials. By way of example, for one collection of Pinus radiata, 28 different cell lines clones) produced 6066 mature cotyledonary stage embryos. Of these 2980 plants were successfully established in soil, giving an average conversion of 49.1%. The best conversion of mature somatic embryos to plants in soil was 73% (1001 plants from 1367 somatic embryos). Plants from somatic embryos of Pinus taeda have also been transferred to soil by the same process.

EXAMPLE 8 EFFECTIVE RANGE OF CONCENTRATIONS OF PREFERRED MEDIUM MINERAL ELEMENTS

Similar experiments to Examples 1–4 and 7 were carried out using ion concentrations, 0.125, 0.25, 0.5, 1.0, 1.5 and 2.0 times those of the preferred medium of Table 3 at each developmental stage and also for embryo germination. The results are presented in Table 8. The concentrations of components other than inorganic ions is the same for each of the six different strength solutions and appropriate for the step being investigated. The concentration of the other components are those used in Examples 1–4 and 7 for the particular step being investigated.

TABLE 8

Effective range of concentration of preferred medium mineral elements
Stage of Development

|  | ETC (1) | ETP (2) | EDM (3) | EM#1 (4) | EM#2 (5) | EG (6) |
|---|---|---|---|---|---|---|
| 1/8 strength* | − | − | − | − | − | − |
| 1/4 strength | − | − | − | − | − | − |
| 1/2 strength | +++ | ++ | ++ | + | + | +++ |
| Full strength | + | +++ | +++ | +++ | +++ | ++ |
| 1.5 × strength | − | + | + | + | + | + |
| 2 × strength | − | − | − | − | − | − |

ETG = Embryogenic Tissue Capture
ETP = Embryogenic Tissue Proliferation on Standard Embryogenesis Medium
EDM = Embryogenic Development on Development Medium
EM#1 = Embryo Maturation #1
EM#2 = Embryo Maturation #2
EG = Embryo Germination
* does not gel
+++ optimal growth
++ useful growth
+ slower growth
− not effective This table represents the effective range of concentration of preferred medium mineral elements for *Pinus radiata*. The concentrations giving the best result (+++) for *Pinus radiata* also gave good results for *Pinus taeda* at every stage, for *Pinus elliotii* for the first 3 stages, and for *Pseudotsuga menziesii* for the first 4 stages.

MEDIA FOR EMBRYOGENIC TISSUE CAPTURE, MAINTENANCE, DEVELOPMENT, AND MATURATION

TABLE A1

Major Ion Stock:

| Compound | Weight gm |
|---|---|
| $KNO_3$ | 14.31 |
| $MgSO_4 \cdot 7H_2O$ | 4.00 |
| $CaCl_2 \cdot 2H_2O$ | 0.25 |
| $NaNO_3$ | 3.10 |
| $NH_4H_2PO_4$ | 2.25 |
| make up to 400 ml | |

TABLE A2

Minor Ion Stock

| Compound | Weight mg |
|---|---|
| $MnSO_4 \cdot 4H_2O$ | 36.0 |
| $H_3BO_3$ | 80.0 |
| $ZnSO_4 \cdot 7H_3O$ | 250.0 |
| KI | 10.0 |
| $CuSO_4 \cdot 5H_2O$ | 24.0 |
| $Na_2MoO_4 \cdot 2H_2O$ | 2.0 |
| $CoCl_2 \cdot 6H_2O$ | 2.0 |
| make up to 200 ml | |

TABLE A3

Iron stock - to make 1 liter

| | |
|---|---|
| $FeSO_4 \cdot 7H_2O$ | 1.5 gm |
| $Na_2EDTA$ | 2.0 gm |

TABLE A4

Vitamin stock - to make 1 liter

| | |
|---|---|
| Thiamine HCl | 0.5 gm |
| Nicotinic acid | 0.5 gm |
| Pyridoxine HCl | 0.05 gm |

TABLE A5

Standard Embryonic Tissue Capture Medium

| | per liter of medium |
|---|---|
| major ion stock | 20 ml |
| minor ions stock | 10 ml |
| Iron chelate stock | 10 ml |
| Vitamin stock | 5 ml |
| Inositol | 0.5 gm |
| Sucrose | 10.0 gm |
| Charcoal (Merck, activated) | 2.0 gm |
| Difco Bacto agar | 8.0 gm | pH adjust to 5.6–5.8 before addition of agar and autoclaving

TABLE A6

Standard Embryogenesis Medium (embryogenic tissue maintenance medium)

| | per liter of medium |
|---|---|
| Major ion stock | 40 ml |
| Minor ion stock | 20 ml |
| Iron chelate stock | 20 ml |
| Vitamin stock | 10 ml |
| Inositol | 1.0 gm |
| Sucrose | 30.0 gm |
| Difco Bacto agar | 8.0 gm | pH adjust to 5.6–5.8 before addition of agar and autoclaving add the following filter sterilised amino acids after autoclaving:

| major amino acids | milligram per liter |
|---|---|
| glutamine | 110 |
| asparagine | 105 |
| arginine | 35 |
| minor amino acids stock | 2 ml per liter |

TABLE A6b

Minor amino acid stock

| amino acid | gm |
|---|---|
| citrulline | 1.58 |
| ornithine | 1.52 |
| lysine | 1.10 |
| alanine | 0.8 |
| proline | 0.7 |

3.1 Make up to 800 ml with double distilled water.
3.2 Dispense into 40 ml aliquots.
3.3 Freeze immediately, store frozen, and thaw only on day of use.
3.4 Adjust pH to 5.6–5.8 and filter sterilise before use.

TABLE A7

Embryo Development Medium

| | per liter of medium |
|---|---|
| Major ion stock | 40 ml |
| Minor ion stock | 20 ml |
| Iron chelate stock | 20 ml |
| Vitamin stock | 10 ml |
| Inositol | 1.0 gm |
| Sucrose | 30.0 gm |
| Kelco Gelrite | 3.0 gm | pH adjust to 5.6–5.8 before addition of agar and autoclaving.
Add the following filter sterilised amino acids after autoclaving.

| major amino acids | milligram per liter |
|---|---|
| glutamine | 550 |
| asparagine | 510 |
| arginine | 175 |
| minor amino acids stock (as per Table A6b) | 10 ml per liter |

TABLE A8

Embryo Maturation medium #1 (EMM#1)

To make one liter of medium

Step 1

TABLE A8-continued

Embryo Maturation medium #1 (EMM#1)

| To make one liter of medium | |
|---|---|
| Major ion stock | 40 ml |
| Minor ion stock | 20 ml |
| Iron chelate stock | 20 ml |
| Vitamin stock | 10 ml |
| Inositol | 1 gm |
| Sucrose | 30 gm |

Dissolve in double distilled water, and adjust volume to allow for addition of filter sterilised components.
Adjust pH to 5.7
Add Gelrite 3 gm per 500 ml flask (6 gm per liter) then add pH adjusted liquid.
Autoclave.
Step 2

| Dissolve with heating to give final volume of 50 ml | |
|---|---|
| Minor amino acid stock | 40 ml |
| Glutamine | 7.3 gm |
| Asparagine | 2.1 gm |
| Arginine | 0.7 gm |
| Abscisic Acid | 15 mg |
| (dissolve in 1N NaOH) | |
| Filter sterilise and add to autoclaved medium | |

TABLE A9

Embryo Maturation Medium #2 (EMM#2)

Prepare as for EMM#1
Substitute Gelrite 2.25 gm per 500 ml flask (4.5 gm per liter)

TABLE A10

Embryo Germination Medium (NZRI EGM)

| | Per liter of medium |
|---|---|
| Major ion stock | 24 ml |
| Minor ion stock | 12 ml |
| Iron chelate stock | 12 ml |
| Vitamin stock | 6 ml |
| Inositol | 0.6 gm |
| Glucose | 30 gm |
| Gelrite | 5.0 gm |

Adjust to pH 5.70 and autoclave
Add filter sterilised amino acids in aqueous solution adjusted to pH 5.70
| Arginine | 0.26 gm |
|---|---|
| Glutamine | 0.40 gm |
| Proline | 0.02 gm |

Aspects of the present invention have been described by way of example only and it should be appreciated that modifications and additions may be made thereto without departing from the scope of the invention.

References Cited:

Gupta, P. K., Pullman G. S., 1990: *Method for reproducing coniferous plants by somatic embryogenesis*. U.S. Pat. No. 4,957,866, Sep. 18, 1990.

Gupta, P. K., Pullman G. S., 1991a: *Method for reproducing coniferous plants by using somatic embryogenesis using abscisic acid and osmotic potential variation*. U.S. Pat. No. 5,036,007, Jul. 30, 1991.

Gupta, P. K., Pullman G. S., 1991b: *High concentration enrichment of conifer embryonal cells*. U.S. Pat. No. 5,041,382, Aug. 20, 1991.

What is claimed is:

1. A growth medium effective for maintaining conifer embryogenic tissue or for subsequent development, maturation or germination of conifer embryos including inorganic ions in the following concentrations:

| ION | CONCENTRATION RANGE (mmoles/l) |
|---|---|
| $NO_3$ | 8–27 |
| $NH_4$ | 0.95–3 |
| Ca | 0.08–0.25 |
| Fe | 0.05–0.15 |
| Na | 1.9–5.75 |
| Zn | 0.045–0.135 |
| Cu | $4.5 \times 10^{-3}$–$1.5 \times 10^{-2}$ |
| Mg | 0.8–2.5. |

2. A growth medium as claimed in claim 1 including inorganic ions in the concentration ranges:

| ION | CONCENTRATION RANGE (mmoles/l) |
|---|---|
| $NO_3$ | 13–23 |
| $NH_4$ | 1.5–2.5 |
| Ca | 0.12–0.21 |
| Fe | 0.07 0.13 |
| Na | 2.9–4.9 |
| Zn | 0.06–0.12 |
| Cu | $7 \times 10^{-3}$–$1.2 \times 10^{-2}$ |
| Mg | 1.2–2.0. |

3. A growth medium as claimed in claim 1 which is free of the or does not depend on the use of plant growth regulators (hormones, phytohormones) of the auxin and/or cytokinin type.

4. A growth medium effective for sustaining the growth of conifer embyogenic tissue or for the development or maturation of conifer embryos including inorganic ions in the concentrations:

| ION | CONCENTRATION (mmoles/l) |
|---|---|
| $NO_3$ | about 17.8 |
| $NH_4$ | about 1.96 |
| Ca | about 0.17 |
| Fe | about 0.10 |
| Na | about 3.85 |
| Zn | about 0.09 |
| Cu | about $9.6 \times 10^{-3}$ |
| Mg | about 1.62. |

5. A growth medium as claimed in claim 4 and which is free of or does not depend on the use of plant growth regulators (hormones, phytohormones) of the auxin and/or cytokinin type.

6. A growth medium as claimed in claim 5 including inorganic ions in the concentrations:

| ION | CONCENTRATION (mmoles/l) |
|---|---|
| NO3 | 17.80 |
| NH4 | 1.96 |
| TOTAL N | 19.76 |
| P | 1.96 |
| K | 14.16 |
| Ca | 0.17 |
| Mg | 1.62 |
| Cl | $3.42 \times 10^{-1}$ |

-continued

| ION | CONCENTRATION (mmoles/l) |
|---|---|
| Fe | 0.10 |
| S | 1.83 |
| Na | 3.85 |
| B | 0.13 |
| Mn | $1.62 \times 10^{-2}$ |
| Zn | 0.09 |
| Cu | $9.61 \times 10^{-3}$ |
| Mo | $8.27 \times 10^{-4}$ |
| Co | $8.41 \times 10^{-4}$ |
| I | $6.02 \times 10^{-3}$ |

7. A medium or claim 1 including 5 g/l-50 g/l (w/v) sucrose.

8. A medium of claim 1 including 0.5 g/l-1.5 g/l (w/v) agar.

9. An embryo maturation medium of claim 1 further including 4 to 9 grams gellan gum per liter.

10. An embryo maturation medium of claim 1 further including 5 to 7 grams per liter gellan gum.

11. A medium of claim 1 including glutamine and at least one other amino acid selected from asparagine, arginine, citrulline, ornithine, lysine, alanine and proline.

12. A medium of claim 1 including sucrose, gellan gum, glutamine and at least one amino acid chosen from asparagine, arginine, citrulline, ornithine, lysine, alanine and proline.

13. A medium of claim 12 including 5 milligrams per liter to 25 milligrams per liter of abscisic acid.

14. A method of growing conifer embryogenic tissue including the step of growing the tissue on a growth medium including inorganic ions in the concentration ranges:

| ION | CONCENTRATION RANGE (mmoles/l) |
|---|---|
| $NO_3$ | 8–27 |
| $NH_4$ | 0.95–3 |
| Ca | 0.08–0.25 |
| Fe | 0.05–0.15 |
| Na | 1.9–5.75 |
| Zn | 0.045–0.135 |
| Cu | $4.5 \times 10^{-3}$–$1.5 \times 10^{-2}$ |
| Mg | 0.8–2.5. |

15. A method of growing conifer embryogenic tissue including the step of placing whole megagametophytes containing embryos at the polyembryogenesis stage onto a growth medium including inorganic ions in the concentration ranges:

| ION | CONCENTRATION RANGE (mmoles/l) |
|---|---|
| $NO_3$ | 8.9–17.8 |
| $NH_4$ | 0.98–1.96 |
| Ca | 0.085–0.17 |
| Fe | 0.05–0.10 |
| Na | 1.925–3.85– |
| Zn | 0.045–0.09 |
| Cu | $4.8 \times 10^{-3}$–$9.61 \times 10^{-3}$ |
| Mg | 0.81–1.62. |

16. A method of capturing conifer embryogenic tissue at the zygotic polyembryogenesis stage including the step of placing whole megagometophytes on a medium including ions at concentrations shown below:

| ION | CONCENTRATION (mmoles/l) |
|---|---|
| $NO_3$ | about 8.9 |
| $NH_4$ | about 0.98 |
| Ca | about 0.085 |
| Fe | about 0.05 |
| Na | about 1.925 |
| Zn | about 0.045 |
| Cu | about $4.8 \times 10^{-3}$ |
| Mg | about 0.81. |

17. A method as claimed in claim 14, wherein the embryogenic tissue is derived from *Pinus radiata, Pinus taeda, Pinus elliotii* or *Pseudotsuga menziesii*.

18. A method as claimed in claim 16 wherein the embryogenic tissue is derived from *Pinus radiata, Pinus taeda, Pinus elliotti* or *Pseudotsuga menzieii*.

19. A method as claimed in claim 16 wherein the embryogenic tissue is derived from *Pinus radiata*.

20. A method according to claim 14 including promoting/allowing development of cotyledonary tissue at the shoot apex of the embryo on said medium.

21. A method for maintaining embryogenic tissue, or for development or maturation of conifer somatic embryos including the step of growing the tissue on a growth medium including ions in the concentrations as shown below:

| ION | CONCENTRATION (mmoles/l) |
|---|---|
| NO3 | 17.80 |
| NH4 | 1.96 |
| TOTAL N | 19.76 |
| P | 1.96 |
| K | 14.16 |
| Ca | 0.17 |
| Mg | 1.62 |
| Cl | $3.42 \times 10^{-1}$ |
| Fe | 0.10 |
| S | 1.83 |
| Na | 3.85 |
| B | 0.13 |
| Mn | $1.62 \times 10^{-7}$ |
| Zn | 0.09 |
| Cu | $9.61 \times 10^{-3}$ |
| Mo | $8.27 \times 10^{-4}$ |
| Co | $8.41 \times 10^{-4}$ |
| I | $6.02 \times 10^{-3}$. |

22. A method as claimed in claim 20 wherein said conifer is *Pinus radiata*.

23. A method as claimed in claim 20 wherein said conifer is *Pinus radiata, Pinus taeda, Pinus elliotti* or *Pseudotsuga menziesii*.

24. A method according to claim 14 wherein said tissue is cultured in a vessel covered with a water vapour permeable film.

25. A method according to claim 21 wherein said tissue is cultured in a vessel covered with a water vapour permeable film.

26. A method as claimed in claim 24 wherein the film allows the transmission of water vapour at the rate of between 90–150 gm/sq meter per day.

27. A growth medium for capturing conifer embryogenic tissue at the zygotic polyembryogenesis stage including inorganic ions in the following conentrations:

| ION | CONCENTRATION (mmoles/l) |
|---|---|
| $NO_3$ | about 8.9 |
| $NH_4$ | about 0.98 |
| Ca | about 0.085 |
| Fe | about 0.05 |
| Na | about 1.925 |
| Zn | about 0.045 |
| Cu | about $4.8 \times 10^2$ |
| Mg | about 0.81. |

28. A conifer embryo germination medium according to claim 1 including inorganic ions in the following concentrations:

| ION | CONCENTRATION RANGE (mmoles/l) |
|---|---|
| $NO_3$ | 8,9–17.8 |
| $NH_4$ | 0.98–1.96 |
| Ca | 0.085–0.17 |
| Fe | 0.05 0.10 |
| Na | 1.925–3.85 |
| Zn | 0.045–0.09 |
| Cu | $4.8 \times 10^{-3}$–$9.61 \times 10^{-3}$ |
| Mg | 0.81–1.62. |

29. A medium as claimed in claim 28, which is the medium of Table A10.

30. A growth medium of claim 1 for growing conifer embryogenic tissue selected from the media of Tables A5, A6, A7, A8 and A9.

31. A method for growing conifer plants including:

(a) dissecting out megagametaphytes from seeds of cones at the appropriate stage of development of the zygotic embryos;

(b) placing said megagametophytes on a medium as claimed in claim 27;

(c) growing embryogenic tissue for up to a month on said medium;

(d) transferring the embryogenic tissue to a second growth medium including inorganic ions in the concentrations:

| ION | CONCENTRATION (mmoles/l) |
|---|---|
| $NO^3$ | 17.80 |
| $NH^4$ | 1.96 |
| TOTAL N | 19.76 |
| P | 1.96 |
| K | 14.16 |
| Ca | 0.17 |
| Mg | 1.62 |
| Cl | $3.42 \times 10^{-1}$ |
| Fe | 0.10 |
| S | 1.83 |
| Na | 3.85 |
| B | 0.13 |
| Mn | $1.62 \times 10^{-2}$ |
| Zn | 0.09 |
| Cu | $9.61 \times 10^{-3}$ |
| Mo | $8.27 \times 10^{-4}$ |
| Co | $8.41 \times 10^{-4}$ |
| I | $6.01 \times 10^{-3}$ |

(e) transferring the embryogenic tissue to a third medium including inorganic ions in the concentrations of the second medium and further including about 550 mg/l glutamine and one more of asparagine, arginine, citrulline, ornithine, lysine, alanine and proline, said third medium being gelled with gellan gum;

(f) transferring the embryogenic tissue to a fourth medium which is an embryo maturation medium including inorganic ons in the concentrations of the second medium and further including 50–10 gm/l glutamine, one or more of asparagine, arginine, citrulline, ornithine, lysine, alanine, and proline, 5–25 mg/l abscisic acid and 4–9 gm/l gellan gum;

(g) harvesting mature cotyledonary stage embryos;

(h) germinating said cotyledonary stage embryos; and (i) transferring to soil.

32. A process for producing a conifer plant including the steps of growing conifer embryogenic tissue by the method of claim 14, obtaining mature cotyledonary stage embryos, and germinating said cotyledonary stage embryos.

33. A method of claim 31, in which said conifer is *Pinus radiata* or *Pinus taeda*.

34. A method of claim 32, in which said conifer is *Pinus radiata* or *Pinus taeda*.

* * * * *